United States Patent
Lizzi et al.

(10) Patent No.: US 9,410,185 B2
(45) Date of Patent: Aug. 9, 2016

(54) DISSOLVABLE FILMS AND METHODS INCLUDING THE SAME

(71) Applicant: Becton, Dickinson and Company, Franklin Lakes, NJ (US)

(72) Inventors: Michael Lizzi, Stewartstown, PA (US); Donald Copertino, Catonsville, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 14/220,598

(22) Filed: Mar. 20, 2014

(65) Prior Publication Data
US 2014/0205996 A1 Jul. 24, 2014

Related U.S. Application Data

(63) Continuation of application No. 11/165,325, filed on Jun. 24, 2005, now Pat. No. 9,267,167.

(60) Provisional application No. 60/582,821, filed on Jun. 28, 2004.

(51) Int. Cl.
| | |
|---|---|
| *G01N 33/553* | (2006.01) |
| *G01N 33/52* | (2006.01) |
| *B01L 3/00* | (2006.01) |
| *B05D 7/22* | (2006.01) |
| *B65D 83/00* | (2006.01) |
| *C12Q 1/68* | (2006.01) |
| *B03C 1/01* | (2006.01) |
| *B03C 1/28* | (2006.01) |
| *G01N 35/00* | (2006.01) |

(52) U.S. Cl.
CPC .............. *C12Q 1/6806* (2013.01); *B01L 3/502* (2013.01); *B01L 3/5082* (2013.01); *B01L 3/52* (2013.01); *B03C 1/01* (2013.01); *B03C 1/286* (2013.01); *C12Q 1/689* (2013.01); *C12Q 1/6846* (2013.01); *B01L 3/5085* (2013.01); *B01L 2200/026* (2013.01); *B01L 2200/0642* (2013.01); *B01L 2200/16* (2013.01); *B01L 2300/0829* (2013.01); *B01L 2400/0677* (2013.01); *B03C 2201/26* (2013.01); *G01N 2035/00277* (2013.01); *Y10T 436/25* (2015.01); *Y10T 436/255* (2015.01)

(58) Field of Classification Search
None
See application file for complete search history.

(56) References Cited

U.S. PATENT DOCUMENTS

| | | | |
|---|---|---|---|
| 2,047,398 A | 7/1936 | Voss et al. | |
| 3,431,166 A | 3/1969 | Musani et al. | |
| 3,985,649 A | 10/1976 | Eddelman | |
| 4,356,149 A | 10/1982 | Kitajima et al. | |
| 4,373,466 A | 2/1983 | MacPhee | |
| 4,387,164 A | 6/1983 | Hevey et al. | |
| 4,456,628 A | 6/1984 | Bauer et al. | |
| 4,522,923 A | 6/1985 | Deutsch et al. | |
| 4,612,247 A | 9/1986 | Walsh et al. | |
| 4,654,395 A | 3/1987 | Schulz et al. | |
| 4,797,221 A | 1/1989 | Gueldenzopf | |
| 4,891,319 A | 1/1990 | Roser | |
| 5,125,534 A | 6/1992 | Rose et al. | |
| 5,206,026 A | 4/1993 | Sharik | |
| 5,284,659 A | 2/1994 | Cherukuri et al. | |
| 5,350,676 A | 9/1994 | Oberhardt et al. | |
| 5,354,551 A | 10/1994 | Schmidt | |
| 5,508,367 A | 4/1996 | Zajaczkowski | |
| 5,529,782 A | 6/1996 | Staab | |
| 5,536,470 A | 7/1996 | Frey et al. | |
| 5,629,003 A | 5/1997 | Horstmann et al. | |
| 5,707,860 A | 1/1998 | Collis et al. | |
| 5,750,333 A | 5/1998 | Clark | |
| 5,756,049 A * | 5/1998 | Brayton | 422/430 |
| 5,840,878 A | 11/1998 | Collis et al. | |
| 5,962,310 A | 10/1999 | Collis et al. | |
| 5,973,138 A | 10/1999 | Collis | |
| 6,004,820 A | 12/1999 | Brayton | |
| 6,036,971 A | 3/2000 | Kimoto et al. | |
| 6,077,502 A | 6/2000 | Witt et al. | |
| 6,174,546 B1 | 1/2001 | Therriault et al. | |
| 6,204,033 B1 | 3/2001 | Muller-Schulte | |
| 6,235,491 B1 | 5/2001 | Connolly | |
| 6,274,386 B1 | 8/2001 | Harttig | |
| 6,368,595 B2 | 4/2002 | Edens et al. | |
| 6,387,486 B1 | 5/2002 | Malik et al. | |

(Continued)

FOREIGN PATENT DOCUMENTS

| | | |
|---|---|---|
| CN | 1095033 | 11/1994 |
| CN | 1134450 A | 10/1996 |

(Continued)

OTHER PUBLICATIONS

Adhesives Research Inc., "Portfolio of ARcare@ Pressure Sensitive Adhesive Technologies for Healthcare Applications", printed 2002.

(Continued)

*Primary Examiner* — Galina Yakovleva

(74) *Attorney, Agent, or Firm* — Lerner, David, Littenberg, Krumholz & Mentlik, LLP

(57) ABSTRACT

A method includes providing a container, introducing a substance into the container, and introducing a readily dissolvable film into the container such that the dissolvable film overlies the substance within the container. An alternative method includes providing a container, providing a readily dissolvable film, the film comprising a substance carried by the film, and introducing the film into the container.

20 Claims, 6 Drawing Sheets

(56) References Cited

U.S. PATENT DOCUMENTS

| | | |
|---|---|---|
| 6,419,903 B1 | 7/2002 | Xu et al. |
| 6,433,160 B1 | 8/2002 | Collis |
| 6,436,635 B1 | 8/2002 | Fu et al. |
| 6,527,762 B1 | 3/2003 | Santini, Jr. et al. |
| 6,531,094 B2 | 3/2003 | Seto et al. |
| 6,613,528 B2 | 9/2003 | Helbert et al. |
| 6,672,458 B2 | 1/2004 | Hansen et al. |
| 6,720,191 B1 * | 4/2004 | Goldstein et al. ............. 436/174 |
| 6,726,054 B2 | 4/2004 | Fagen et al. |
| 6,923,981 B2 | 8/2005 | Leung et al. |
| 6,946,501 B2 | 9/2005 | Kochvar et al. |
| 6,995,137 B2 | 2/2006 | You et al. |
| 2001/0001669 A1 | 5/2001 | DeVore et al. |
| 2001/0046714 A1 | 11/2001 | Harttig |
| 2002/0106686 A1 | 8/2002 | McKernan |
| 2002/0131990 A1 | 9/2002 | Barkalow et al. |
| 2002/0138154 A1 | 9/2002 | Li et al. |
| 2002/0161088 A1 | 10/2002 | Kochvar et al. |
| 2003/0082587 A1 | 5/2003 | Seul et al. |
| 2003/0228411 A1 | 12/2003 | Tai et al. |
| 2004/0043061 A1 | 3/2004 | Leon et al. |
| 2004/0065578 A1 | 4/2004 | Bone et al. |
| 2004/0086539 A1 | 5/2004 | Pinna et al. |
| 2004/0157218 A1 | 8/2004 | Collis et al. |
| 2004/0157219 A1 | 8/2004 | Lou et al. |
| 2005/0070701 A1 | 3/2005 | Hochstetler et al. |
| 2005/0118217 A1 | 6/2005 | Barnhart et al. |
| 2005/0208110 A1 | 9/2005 | Singh et al. |
| 2005/0287682 A1 * | 12/2005 | Lizzi et al. .................... 436/526 |
| 2006/0078466 A1 | 4/2006 | Colin et al. |
| 2014/0205996 A1 | 7/2014 | Lizzi et al. |

FOREIGN PATENT DOCUMENTS

| | | |
|---|---|---|
| EP | 0514172 A1 | 11/1992 |
| EP | 0560099 A2 | 9/1993 |
| EP | 1018648 A1 | 7/2000 |
| JP | 55-30976 | 7/1980 |
| JP | 60-105963 A | 6/1985 |
| JP | 61270650 | 11/1986 |
| JP | 04023988 A | 1/1992 |
| JP | 09061311 | 3/1997 |
| JP | 09502521 A | 3/1997 |
| JP | 09131174 | 5/1997 |
| JP | 10-062422 A | 3/1998 |
| JP | 2001518284 A | 10/2001 |
| JP | 2002511926 | 4/2002 |
| JP | 2003502653 | 1/2003 |
| JP | 2004354311 | 12/2004 |
| WO | 93/08095 A1 | 4/1993 |
| WO | 94/24211 A1 | 10/1994 |
| WO | 9506868 A1 | 3/1995 |
| WO | 96/08555 A1 | 3/1996 |
| WO | 96/14365 A2 | 5/1996 |
| WO | 9641811 A1 | 12/1996 |
| WO | 97/00282 A1 | 1/1997 |
| WO | 9848282 A1 | 10/1998 |
| WO | 99/34774 A1 | 7/1999 |
| WO | 99/45050 A1 | 9/1999 |
| WO | 99/61047 A1 | 12/1999 |
| WO | 0078452 A1 | 12/2000 |
| WO | 02/008380 A1 | 1/2002 |
| WO | 02/074238 A2 | 9/2002 |
| WO | 03/003957 A1 | 1/2003 |
| WO | 03/027991 A1 | 4/2003 |
| WO | 03/040360 A1 | 5/2003 |
| WO | 03/054077 A1 | 7/2003 |
| WO | 03/076513 A1 | 9/2003 |
| WO | 2004/031271 A2 | 4/2004 |
| WO | 2004/078350 A2 | 9/2004 |
| WO | 2005/039499 A2 | 5/2005 |
| WO | 2005/040228 A2 | 5/2005 |

OTHER PUBLICATIONS

Dupont, "Hansen Solubility Parameter System" Published Dec. 2000 Pub. No. H-85303-2.

International Search Report and Written Opinion for PCT/US2005/023058, filed Mar. 6, 2007.

Solomons, "Organic Chemistry", 4th Edition, 1988, John Wiley & Sons, New York, NY, p. 519.

Parker, "Cool Mint Listerine PocketPaks", Nov. 29, 2001, http://www.everything.com/index.pl?nodejd=1208151.

Office Action from Australian Application No. 2005327516, dated Dec. 10, 2010.

European Search Report, EP 11166252, dated Dec. 23, 2011.

Japanese Office Action for Application No. JP 2007-519383 dated Feb. 28, 2012.

* cited by examiner

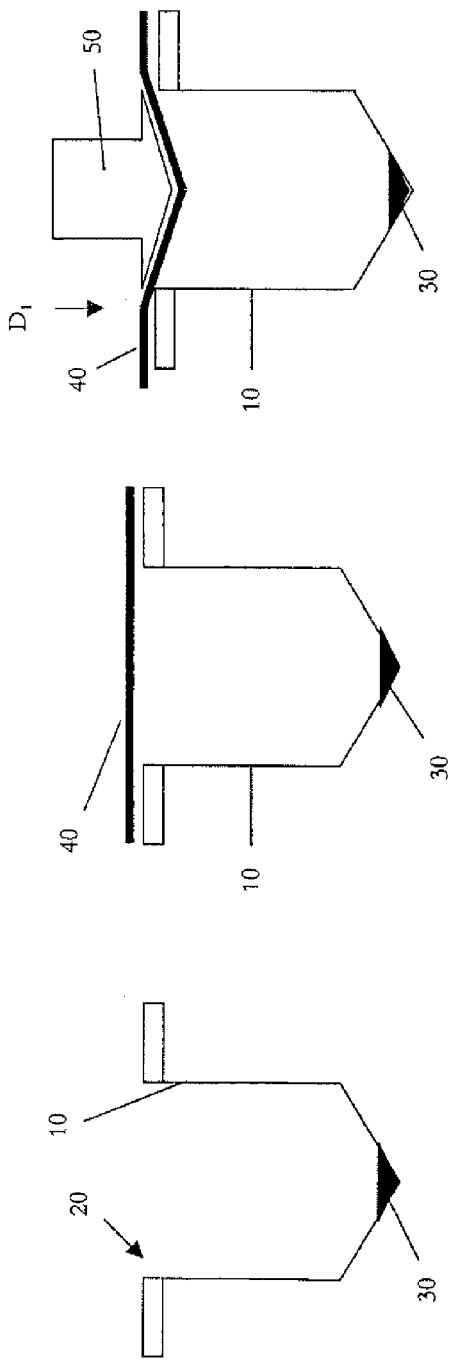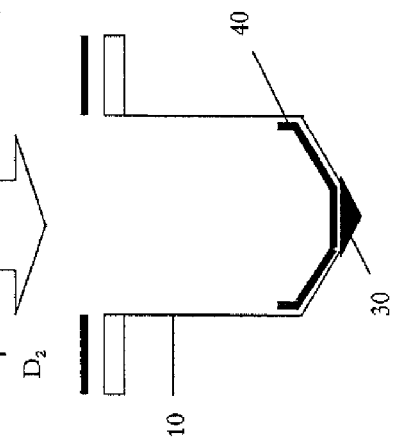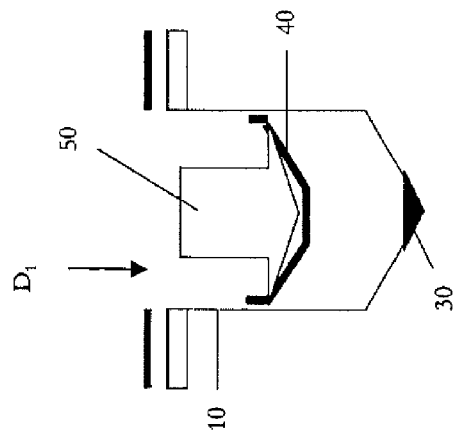

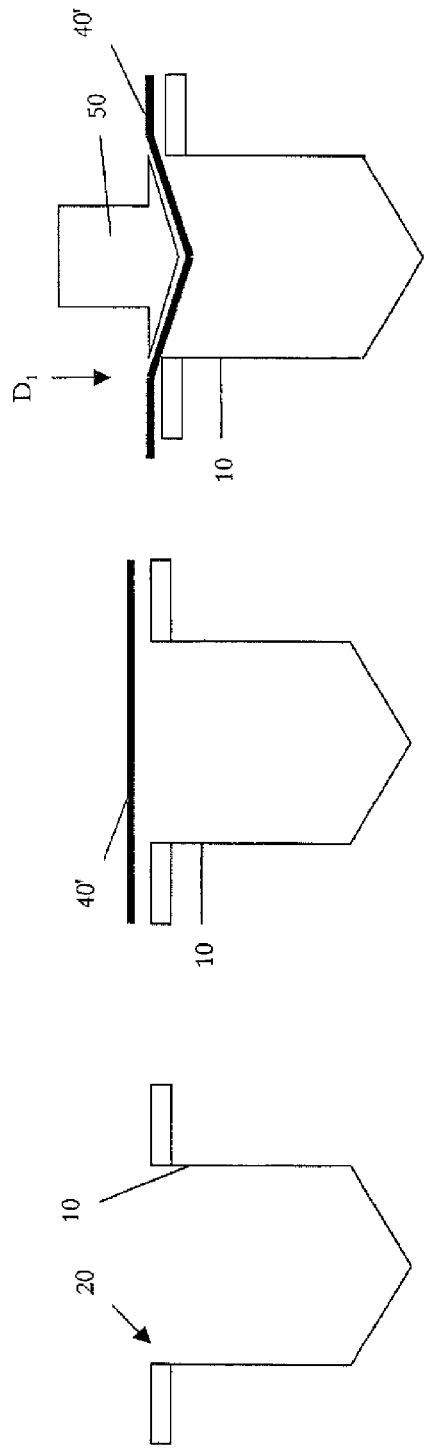
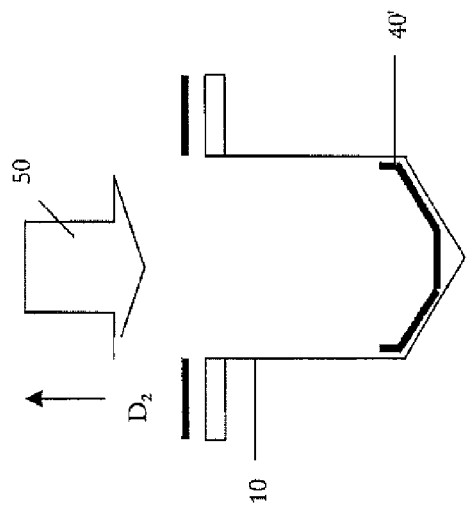
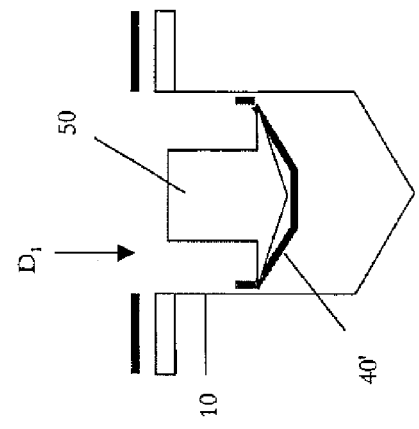
FIG. 2A
FIG. 2B
FIG. 2C
FIG. 2D
FIG. 2E

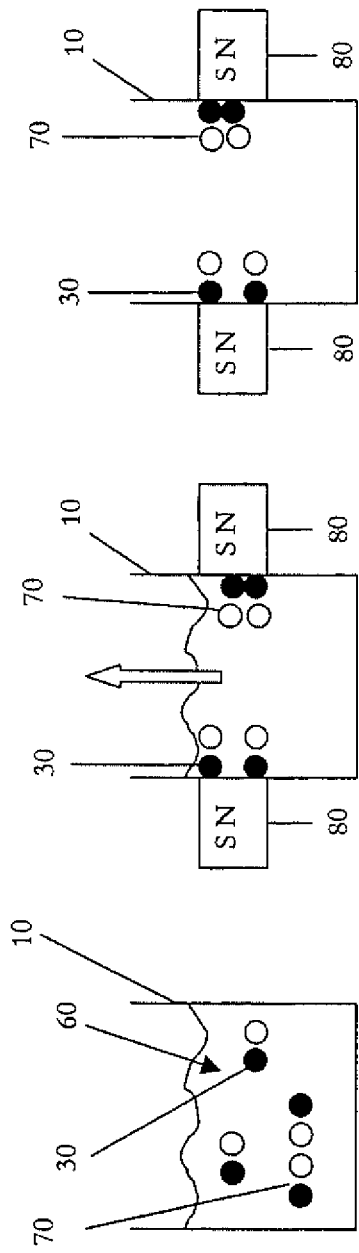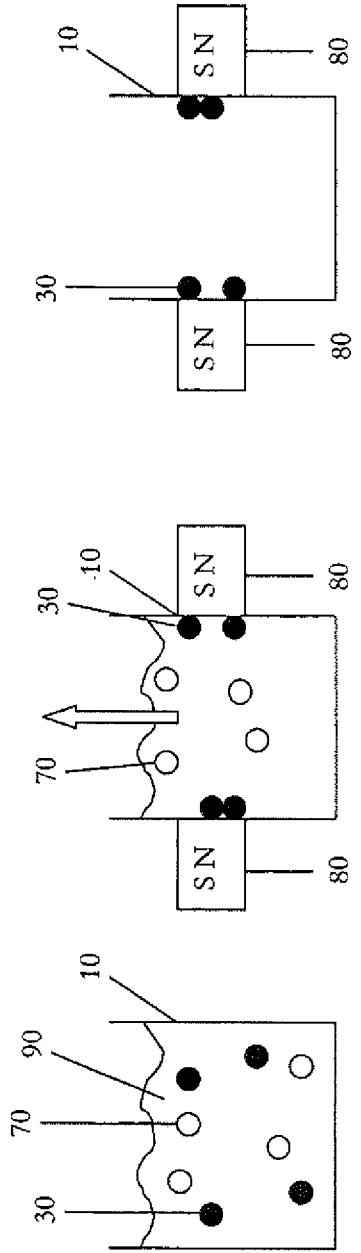

DISSOLVABLE FILMS AND METHODS INCLUDING THE SAME

RELATED APPLICATIONS

This application is a continuation of U.S. application Ser. No. 11/165,325, filed Jun. 24, 2005, which claims priority to U.S. Provisional Application Ser. No. 60/582,821, filed Jun. 28, 2004, the disclosures of which are herein incorporated by reference in their entirety.

FIELD OF THE INVENTION

The present invention is directed to dissolvable membranes or films and methods incorporating the same. For example, the present invention is directed to arrangements including a container, a substance and a dissolvable membrane, as well as methods incorporating the same.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

There are many scientific and industrial arrangements and processes that involve the introduction of fairly precise amounts of one or more substances into a container. Depending on various factors such as the nature of the substance introduced, the construction and properties of the container, as well as the technique used to introduce these substances, it is a common occurrence that some of a substance introduced into the container sticks to the walls of the container in a manner that prevents it from being combined and/or interacting with other substances in the container. When the nature of the process calls for precise amounts of the various substances to be combined, the above-described "sticking" problem can have a significant and undesirable impact on the desired outcome of the process.

In addition, while automation is desirable in the introduction of substances, it can prove difficult to precisely deliver small quantities of substances. Thus, when precise amounts of substances are called for, it is a common practice to measure and introduce these substances into a container by hand. This labor intensive procedure is clearly less than ideal from an efficiency stand point.

One example of the type of scientific or industrial process referred to above is the isolation and/or separation of biological components from a sample. One way of accomplishing this isolation and/or separation involves introducing a biological sample, magnetizable particles, and possibly other substances into a tube, usually gravimetrically or via a pipette. One or more of the biological components present in the tube become associated with the magnetizable particles. Magnets are then caused to come into close proximity to the tube wall(s) causing the magnetizable particles, with the biological component(s) attached thereto, to be drawn to the wall(s) of the tube. The remainder of the constituents present in the tube can then be removed, thereby separating the biological component(s). Various further process steps can be employed to achieve a desired objective.

The walls of the tube and the pipette tip often possess a surface charge that can attract substances thereto. Thus, for example, the introduction of magnetizable particles into the tube poses the above-described problem in that they can often stick to the walls of the tube or pipette in a way that prevents them from properly associating themselves with the rest of the constituents in the tube. Moreover, even if care is taken to prevent the sticking problem when the particles are first introduced, subsequent movement of the tube with the particles contained therein can cause the particles to be thrown against, and stick to, the walls of the tube. Since processes such as the one described above often involve small sample sizes and/or rely upon precise amounts of the various substances to mix together in order to produce a desirable or accurate result, the sticking phenomenon poses a significant problem in the accuracy and reliability in such isolation and/or separation techniques.

Therefore, there is a need in the art, in general to provide arrangements and methods that facilitate more accurate introduction and association of substances within a container. There is also a need in the art for arrangements and methods that promote more accurate and efficient introduction and association of substances involved in the isolation and/or separation of biological components from a sample.

SUMMARY OF THE INVENTION

The present invention satisfies the above-described needs, and others, by providing arrangements and methods that reduce, if not eliminate, sticking of one or more substances to a wall of a container in a way that prevents its proper association with other substances and constituents within the container. The present invention also provides arrangement and techniques that facilitate automation. The present invention additionally provides arrangements and methods that allow for a precise quantity of a substance to be introduced into a container.

According to one aspect, a method of the present invention comprises: (i) providing a container; (ii) introducing the first substance into the container; and (iii) introducing a readily dissolvable film into the container such that the dissolvable film overlies the first substance within the container.

According to a further aspect, the present invention comprises: (i) providing a container; (ii) providing a readily dissolvable film, the first substance carried by the film; and (iii) introducing the film into the container.

According to another aspect of the present invention, either of the above-described methods may further include adding a second substance to the container, and one or more of the following: (v) dissolving the film; and (vi) creating a mixture comprising the first and second substances; (vii) binding the first substance and the second substance together thereby forming a complex; (viii) applying a magnetic field to the container, thereby attracting the complex to a designated area of the container; (ix) removing at least a portion of the biological sample from the container; (x) removing the magnetic field from the container; (xi) disassociating the first substance and second substance from one another; (xii) reapplying the magnetic field to the container thereby attracting the first substance to a designated area of the container; (xiii) removing the second substance from the container; (ix) performing an amplification procedure on the second substance; and (x) conducting an assay to detect the presence and/or concentration of a target analyte in the second substance. One or more of the aforementioned steps may be performed by an automated robotic device.

According to an additional aspect, the present invention provides a kit, comprising: i) a container; ii) a first substance within the container; and iii) a readily dissolvable film within the container and overlaying the first substance. According to yet another aspect, the present invention provides a kit for performing an assay, comprising: i) a container; and ii) a first substance carried by a readily dissolvable film.

BRIEF DESCRIPTION OF THE DRAWINGS

The foregoing and other features, aspects and advantages of the present invention will become apparent from the following description, appended claims and the exemplary embodiments shown in the drawings, which are briefly described below. It should be noted that, unless otherwise specified, like elements have the same reference numbers.

FIGS. 1A-1G are schematic illustrations of processes and arrangements according to the principles of a first aspect of the present invention.

FIGS. 2A-2G are schematic illustrations of processes and arrangements according to the principles of a second aspect of the present invention.

FIGS. 3A-3F are schematic illustrations of further processes and arrangements practicable by implementation of the principles of the present invention.

DETAILED DESCRIPTION OF THE INVENTION

Figure 1G:
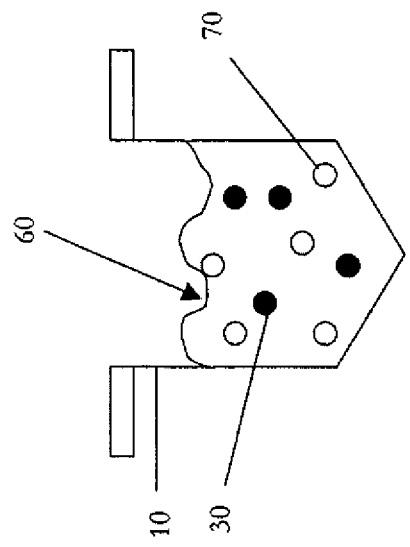

The principles of the present invention will now be further described by the following discussion of certain illustrative embodiments thereof and by reference to the foregoing drawing figures.

As used herein, "biological sample" means any substance comprising bodily fluid or matter including, but not limited to, blood, plasma, serum, urine, bone marrow aspirates, cerebral spinal fluid, tissue, cells, food, feces, saliva, hair, oral secretions, nasal secretions, buccal cells, bronchial lavage, cervical fluids, lymphatic fluids, sputum, and swabs containing any of the foregoing. The above-referenced bodily fluid or matter may be collected from any source. For example, the source is not limited to humans.

As used herein, "magnetically-responsive particle" means a particle is capable of having a magnetic moment imparted thereto or otherwise moveable under the action of a magnetic field.

As used herein, "overlies" means an orientation that, during ordinary usage or field of reference, is vertically above the referenced object or substance.

As used herein, "readily dissolvable" refers to the capability of a material or film to be broken down when contacted by a selected substance(s) at a rate, and to an extent, such that the material can be readily utilized in a desired scientific or industrial process without causing undue delay. For example, "readily dissolvable" means the Hansen parameters for a chosen solvent lie within the solubility volume or area for the material, as plotted on a Hansen solubility map. See, e.g., "Hansen Solubility Parameter System," DuPont Nylon Intermediates and Specialties, publication W-400473, 12/2000.

As used herein, "non-specifically bound" means a binding mechanism that does not occur via a receptor, capture agent, or the like, which would selectively couple with a specific target substance.

As used herein, "specifically bound" means a binding mechanism that occurs via a receptor, capture agent, or the like, which would selectively couple with a specific target substance.

As used herein, "film" means a member with opposing major surfaces. The term "film" is not intended to be limited to a particular geometry or shape. For example, it is contemplated by the present invention that the film can be substantially planar, or may be provided in the shape of a solid or hollow polygon, sphere, or oblong body. The terms "film" and "membrane" are used interchangeably herein.

As previously described, the present invention is directed to a readily dissolvable film and methods incorporating the same. The dissolvable film utilized by the present invention can have any suitable composition so long as it achieves the functional objectives described herein. The readily dissolvable film of the present invention can be formed, at least in part, from known dissolvable substances. For example, any organic or inorganic polymeric material, or a material derived from one or more such materials, characterizable as readily dissolvable could be utilized. Such substances may include cellulose based or derived materials such as low viscosity hydroxyalkylmethyl cellulose or carboxymethyl cellulose. Other suitable materials may include a combination of carboxylic hydroxyalkyl ester monomer with an ethoxylated or propoxylated hydroxyalkyl (meth)acrylate, polyethylene glycol (PEG), and polyvinyl alcohol (PVA). Formulations containing various amounts or combinations of the above-mentioned substances are also contemplated.

Such known substances are utilized, for example, to make dissolvable films that are used as carriers for breath-freshening agents. One such film is described in U.S. Pat. No. 6,419,903, the entire content of which is incorporated herein by reference. The film described therein is generally composed of a combination of a low viscosity hydroxyalkylmethyl cellulose, starch and a flavoring agent. Films utilized in connection with the present invention may optionally omit components such as flavoring, coloring, anti-bacterial and breath-freshening agents.

Films suitable for use in conjunction with the present invention can be made by techniques familiar to those of in the art, such as the technique described in U.S. Pat. No. 6,419,903. A suitable technique generally involves forming a solution or slurry containing the constituent components of the film, casting and drying the solution or slurry to form a film. Once dried the film may be cut into segments. Alternatively, the film can be continuously cast and accumulated in roll form. An optional technique for incorporating substances or components into the film can involve producing a film by any suitable technique, and incorporating a component or substance into the film via a surface application technique. For example, the film may be in a state wherein it is not completely dried or cured, the component or substance is then introduced onto the surface thereof, and the drying or curing process completed. The resulting film comprises the component on or near the surface of the film. Modifications of this technique are also possible. For example, a fully dried or cured film may form the starting material. The dried or cured film may then be subjected to a process such as heating or wetting, such that the surface is modified to more readily accept the component or substance. The component or substance can then be added to the modified surface and the film dried or cooled to render a film comprising the component or substance incorporated therein at the surface of the film. Alternatively, a substance or additional component may simply be applied to the surface of a fully dried or cured film. One advantage of the present invention is that an amount of a substance to be released from the film and introduced into a surrounding medium and be precisely controlled by controlling the concentration of the substance present in the film, and the size of the piece of film utilized.

Films utilized in connection with the present invention may optionally include a fragrance. In certain processes, such as the analysis of biological samples, the inclusion of a fragrance agent can mask the odor often emitted by such samples, thereby improving the working environment.

It is comprehended by the present invention that any suitable substance can be used or provided in conjunction with the dissolvable film. According to one embodiment, the film is utilized in conjunction with magnetically-responsive particles. In this embodiment, magnetically-responsive particles may be separate from the film, or introduced into the film in any suitable manner. For instance, as previously described, the particles can be introduced into the solution or slurry that forms the film so that upon casting and drying the film comprises magnetically-responsive particles dispersed within, and trapped by, a dissolvable matrix. Alternatively, the particles may be incorporated into the film via any of the surface application techniques of the type described above. Upon dissolution of the film, the magnetic particles are released, and can be, for example, dispersed into a substance or mixture acting as a solvent.

The magnetically-responsive particles can be coated or uncoated, treated or untreated, and/or lack any type of surface modification. The magnetically-responsive particles of the present invention may be designed to specifically or non-specifically bind to a target substance. The magnetically-responsive particles may bind to the target substance via any suitable mechanism, such as electrostatic attraction. Such binding techniques are described, for example, in U.S. Pat. Nos. 5,973,138 and 6,433,160, the entire contents of which are incorporated herein by reference.

Suitable magnetically-responsive particles may be composed of iron oxide in forms such as ferric hydroxide and ferrosoferric oxide, which have low solubility in an aqueous environment. Other iron particles such as iron sulfide and iron chloride may also be suitable for binding to target substances. In addition, the particles may be composed of silica-coated magnetically-responsive particles.

The substance may comprise one or more reagents, such as a lysing agent or protein denaturant, an aprotic solvent, an alkaline agent, or a neutralization buffer. The reagent(s) may be utilized in either liquid or dried-down form. The substance may also comprise one or more reaction components, such as a salt, metal, enzyme, oligonucleotide, primer, additional nucleic acid, or protein. Exemplary salts include EDTA, sodium chloride and potassium chloride. Examples of metals include magnesium, manganese, calcium and other trace metals. In addition, the substance may comprise a stabilization component or media components.

The substance may comprise a material (other than magnetically-responsive particles) that is used to purify, extract, amplify or detect nucleic acids or other biological agents. Such processes and substances are described, for example, in U.S. patent application Ser. Nos. 10/359,179 and 10/359,180, the entire contents of which are incorporated herein by reference. In this regard, the substance may comprise a material used to reversibly bind to a nucleic acid such as silica particles, silica-coated particles, silica coated membranes, silica gel, hydrated and hydroxylated silica surfaces, glass powder, glass fiber mats, glass membranes, zeolites, ceramics, or polymeric particles coated with a metal oxide or iron salt.

It is comprehended by the present invention that a combination of one or more substances may be utilized in conjunction with the readily dissolvable film. For instance, a combination of one or more of the above-described substances may be utilized.

When the substance is in particulate form, the shape of the particles is not critical to the present invention. The particles may be of various shapes including, for example, spheres, cubes, oval, capsule-shaped, tablet-shaped, nondescript random shapes, etc., and may be of uniform shape or non-uniform shape. The particles can also have any suitable size. For example, the particles can have an average diameter ranging from sub-micron dimensions to a few microns.

Having described various embodiments and characteristics of the film utilized in connection with the present invention, various exemplary methods utilizing the same will now be described.

A first embodiment of the present invention is schematically illustrated in FIGS. 1A-1G. As illustrated therein, a container 10 is provided that may comprise a suitable opening 20 therein. The container 10 may take any suitable form. According to the illustrated embodiment, the container 10 can generally be in the form of a tube. However, other constructions are contemplated, such as a microwell or array of microwells, a bottle, or a Petridish. A substance 30 is first introduced into the container (FIG. 1A). The substance 30 can have any suitable composition, such as any of the materials identified above for use in conjunction with the readily dissolvable film. According to one embodiment of the present invention, the substance 30 can comprise magnetically-responsive particles having a composition and form according to the previous description. Any suitable technique may be utilized to introduce substance 30. For example, the substance 30 may be introduced by hand or an automated robotic device.

A readily dissolvable film 40 is then positioned over the opening 20 of the container 10 (FIG. 1B). The film 40 can have any suitable composition and/or construction, such as any of the compositions and/or constructions previously described herein. The film 40 can be in the form of a segment that is long enough to span the opening 20, and preferably extend well beyond the boundaries of the opening 20. Alternatively, the film 40 may be in the form of a "continuous" web or roll of such film that is fed over the opening 20 (not shown). The film 40 is then introduced into the container 10 by any suitable mechanism (FIGS. 1C and 1D). According to one embodiment, the film 40 is introduced into the container 10 by a plunger/punch device 50.

The film 40 is positioned within the container 10. The film 40 can be placed at any appropriate location in the container 10. According to the illustrated embodiment, the film 40 is placed such that is overlies the substance 30. Any suitable mechanism or technique may be utilized to position the film 40 within the container 10. According to the illustrated embodiment, the film 40 is pushed down into the container 10 by movement of the plunger/punch device 50 in the longitudinal direction indicated as $D_1$ (FIGS. 1C and 1D). Once the film 40 has been properly positioned, the plunger/punch device 50 is withdrawn from the container 10 by withdrawing the plunger/punch device 50 in the opposite longitudinal direction $D_2$ (FIG. 1E). Other techniques or mechanisms for placing the film 40 are contemplated. For example, the film 40 may be cut into a piece having a suitable dimension and gravity-fed into the tube, optionally through a chute or funnel. The film may also be folded prior to being gravity-fed into the tube. According to another alternative, the film is cut to a specific dimension, then fed into the tube by the use of one or more of a vacuum or positive air pressure. For instance the film is cut above the tube and positive air pressure is used to force the cut film down into the tube. Alternatively, the film is cut at a remote location relative to the tube, a suction device employing a vacuum is used to attach to the film and relocate it proximate to the opening of the tube. The vacuum can then be reversed and the film forced down into the tube with positive air pressure.

As shown in the illustrated embodiment, film 40 overlies the substance 30 in a manner such that the substance 30 is substantially trapped in the bottom of the container 10, thereby substantially preventing dislocation of the substance 30 thus preventing an undesirable scattering of the substance 30 along the sidewalls of the container 10 (FIG. 1E).

Figure 1F:
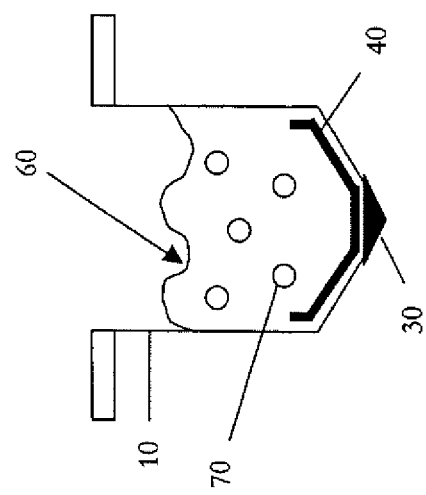

Further optional steps may be performed in the context of the above-described embodiment. For instance, a material or mixture 60 may also be introduced into the container 10 (FIG. 1F). The material or mixture 60 may optionally include a second substance 70. It is contemplated that material or mixture 60 may include other substances, in addition to the second substance 70. The material or mixture 60 as well as the second substance 70 may have any suitable form or composition. According to one embodiment, the material or mixture 60 comprises a biological sample, and the second substance 70 comprises a constituent component thereof, e.g., cells, microorganisms, nucleic acids, proteins, lipids or carbohydrates. The material or mixture 60 acts as a solvent thereby dissolving the film 40. The material or mixture 60 may optionally include one or more added reagents combined therewith. Upon dissolution of the film 40, the substance 30, which was previously trapped against the bottom of the container 10 is freed and can be disbursed within the material or mixture 60 (FIG. 1G).

The description of the previous method, as well as the following description of additional methods, should be read with the understanding that it is contemplated that the methods may consist of, or be limited solely to those steps described herein, that steps in addition to those explicitly described herein may be incorporated into the described methods, that methods comprising subcombinations of the various steps described herein may be practiced, and that methods comprising steps performed in an order different than that described herein may also be practiced. All of these permutations are comprehended by the present invention.

Figure 2G:
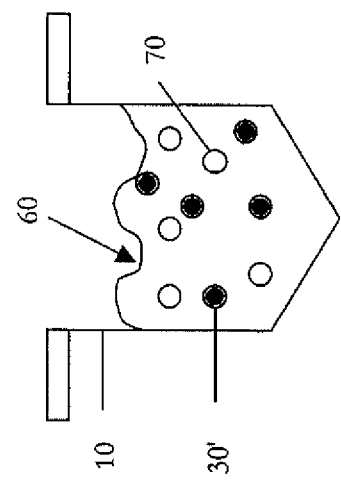

A second embodiment of the present invention is schematically illustrated in FIGS. 2A-2G. Generally speaking, this illustrated embodiment of the present invention is substantially similar to the previously described embodiment. Thus, the constituent components and steps previously described in connection with the first embodiment discussed above should be attributed to the second embodiment as well, unless explicitly noted otherwise in the following description. As illustrated, a suitable container 10 is provided, preferably with an opening 20. A dissolvable film 40' is positioned such that it overlies the opening 20 of container 10 (FIG. 2B). The dissolvable film 40' is substantially similar to the previously described dissolvable film, with the following primary distinction. Namely, the dissolvable film 40' is formed such that a substance 30' is incorporated therein. The substance 30' may be the same as substance 30. As previously noted, a film having this construction can be formed by any suitable technique. For example, a slurry solution can be formed comprising a constituent components of the dissolvable film 40' including substance 30'. Upon casting and drying of the slurry or solution, a dissolvable film 40' is provided which is composed of a dissolvable matrix having substance 30' trapped within, and contained by the dissolvable matrix. Alternatively, the substance 30 may be incorporated into a film by any of the previously described surface application techniques.

The dissolvable film 40' is then introduced and positioned at any suitable location within the container 10 by any suitable mechanism or technique. As illustrated, the dissolvable film 40' may be introduced and positioned by a longitudinally movable plunger/punch device 50. The plunger/punch device 50 is made to travel in a first longitudinal direction $D_1$ (FIGS. 2C and 2D). Once the dissolvable film 40' has been properly positioned within the container 10, the plunger/punch device 50 is withdrawn via movement in the opposite longitudinal direction $D_2$ (FIG. 2E). The film 40' may also be positioned within the container by any of the alternative techniques described above in connection with the first embodiment. As illustrated in FIG. 2E, the dissolvable film 40' is positioned at the bottom of container 10, thereby insuring that the entirety of the film 40' is contacted by additional substances which may be introduced into the container 10.

Figure 2F:
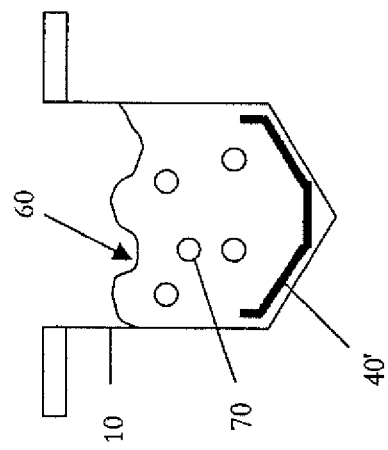

Additional optional steps may also be performed in conjunction with the above-described process. Namely, as described in connection with the first illustrated embodiment, material or mixture 60 may be introduced into the container 10 (FIG. 2F). The material or mixture 60 may optionally include a second substance 70 contained therein. The material or mixture 60 may also optionally include one or more reagents. The material or mixture 60 as well as the second substance 70 may have any suitable composition or form. According to one optional embodiment, the material or mixture 60 comprises biological sample, and the second substance 70 comprises a consistent component thereof, e.g., cells, microorganisms, nucleic acids, proteins, lipids, or carbohydrates. The material or mixture 60 acts as a solvent, thereby breaking apart the dissolvable matrix of the film 40', and releasing the substance 30'. Once released, the substance 30' can be disbursed within the material or mixture 60.

The above-described principles of the present invention can be employed in a number of different scientific and industrial contexts. Generally speaking, the principles of the present invention are useful in any arrangement and/or process in which combinations of accurate amounts of various constituent components are needed or desirable.

One potential application of the principles of the present invention is the isolation and/or separation of constituent components contained in biological samples. In this context, the container 10 comprises an extraction tube, the substance 30 (or 30') comprises magnetically-responsive particles, the material or mixture 60 comprises a biological sample, possibly combined with additional agents or components thereby forming a mixture, and the second substance 70 comprises a constituent component present in the mixture 60, e.g., cells, microorganisms, or nucleic acids.

The methods disclosed above in connection with the description of the embodiments illustrated in FIGS. 1A-1G and FIGS. 2A-2G can be used as the initial stages of such an isolation or separation technique. FIGS. 3A-3F schematically illustrate additional steps which may be performed in conjunction with the previously described steps to carry out an illustrative isolation and/or separation technique. It should be understood that the principles of the present invention can be utilized with numerous types of extraction and/or isolation techniques, and should not be viewed as being limited by the following description of the illustrated embodiment.

The mixture 60, comprising the substance 30 (or 30') and a constituent target component of the biological sample 70, formed as described above, and illustrated, for example, in FIG. 1G and FIG. 2G, is manipulated such that the magnetically responsive particles 30 and the constituent component 70 are bound together, thereby forming a complex (FIG. 3A). Any suitable technique may be utilized to bind the magnetic particles 30 with the constituent component. One such technique involves modification of the pH of the mixture 60, thereby altering the surface attraction properties of the magnetic particles 30 and/or the constituent component 70 such that the mutual attraction therebetween is sufficient to bind the two together. One or more magnets 80 are then brought into close proximity with one or more walls of the container, thereby attracting the above-described complex to the wall(s)

of the container 10 being subjected to the magnetic field by the magnets 80 (FIG. 3B). The remainder of the mixture 60 can then be removed from the container as illustrated in FIG. 3B. The complex may then be subjected to one or more washing steps. Once the remainder has been removed (FIG. 3C) a second material or mixture 90 can then be introduced into the container 10. The second material or mixture 90 can comprise an elution solution or mixture that causes the magnetic particles 30 and the constituent component 70 to disassociate (FIG. 3D). The magnets 80 can then be brought back into close proximity with one or more walls of the container 10, as illustrated in FIG. 3E. The constituent component 70 can then be removed from the container and subjected to further optional processing steps (FIGS. 3E-3F).

Subsequent to the step illustrated in FIG. 3F, constituent component 70 can be subjected to additional processes, such as techniques to detect and/or quantify target analytes. For example, any suitable method of amplification may be used in the methods of the invention. Such methods include, for example, polymerase chain reaction ("PCR"), Strand Displacement Amplification ("SDA"), thermophilic Strand Displacement Amplification ("tSDA"), Self-Sustained Sequence Replication ("3SR"), Nucleic Acid Sequence-Based Amplification ("NASBA"), Qβ replicase systems; Ligase Chain Reaction ("LCR"), and transcription-mediated amplification ("TMA").

Subsequent to cultivation or amplification, an assay may be conducted. For example, an analysis can be performed to determine the presence of pathogens such as *Chlamydia trachomatis* (CT), *Neisseria gonorrhoeae* (GC), *Legionella pneumophila, Mycoplasma pneumoniae, Chlamydiaceae Family*, Herpes Simplex Virus-1, Herpes Simplex Virus-2, Enterovirus, HIV, HCV, HBV, HPV, West Nile Virus, Influenza A, Influenza B, Respiratory Syncytial Virus, *Metapneumovirus, Mycobacterium Avium Complex Direct, Group B Streptococcus, CMV Qualitative, CMV Quantitative, Parainfluenza 1/2/3, Adenovirus, Legionella genus, Legionell micdadei, Bordetella pertussis, Bordetella parapertussis,* Tuberculosis, Tuberculosis Culture Confirmation, *Mycobacterium Avium Complex Culture Confirmation* and *M. Kansasii Culture Confirmation*. Suitable techniques for performing this analysis include the technique embodied in the BDProbeTec™ product manufactured by Becton, Dickinson and Company. Also, genetic testing of nucleic acids present in a sample may be performed.

The above-described steps of FIGS. 1A-1G, 2A-2G and 3A-3F as well as the above-referenced amplification techniques may be carried out manually, in automated fashion or by a combination of manual and automated steps. The automated steps may be performed with an automated robotic device, which optionally includes automated pipetting, mixing, and magnet positioning functionality. The automated robotic device may be computer controlled. For example, the present invention may be utilized in connection with systems and methods of the type described in U.S. Pat. No. 6,672,458, the content of which is incorporated herein by reference in its entirety.

Kits useful in the methods of the present invention comprise at least some of the components already described herein, including for example, a container, a first substance and a readily dissolvable film. In one embodiment, the readily dissolvable film contains the first substance. In an additional embodiment, the first substance and the readily dissolvable film are separate. The kits may optionally contain one or more of the following components previously described herein: reagents; reaction components; stabilization components; media components; magnetically responsive particles; and materials that reversibly bind the nucleic acid. Optionally associated with such kits can be a notice in the form prescribed by a governmental agency regulating the manufacture, use or sale of the products, which notice reflects approval by the agency for manufacture, use or sale for administration. The pack or kit can be a single unit use of the components or it can be a plurality of uses.

The principles of the present invention will now be described by reference to the following illustrative, non-limiting examples.

EXAMPLE 1

An experiment was performed to determine the feasibility of incorporating a dissolvable film into a process of detecting a target analyte. In particular, an assay for *Chlamydia trachomatis* (CT) or *Neisseria gonorrhoeae* (GC) was performed as described below, and an analysis of the effects of the inclusion of dissolvable films into the process was made.

Containers in the form of extraction tubes were provided with magnetically-responsive particles in the form of iron particles according to the following techniques: (1) Approximately 8 mg of magnetically-responsive particles were dispensed into multiple extraction tubes by hand (as a control); (2) Approximately 8 mg of magnetically-responsive particles were pipetted into multiple extraction tube by hand, then covered with a dissolvable film in the form of the following commercially-acquired dissolvable films: (a) Listerine Cool Mint® strips; (b) Listerine Fresh Burst® strips; and (c) Listerine Cinnamon® strips; (3) A dissolvable film formed from a dissolvable carboxymethyl cellulose material loaded with iron oxide particles. The density of the iron oxide particles present in the film is on the order of 8.89 mg/1.5 cm$^2$. This loaded film was then introduced into an extraction tube with a punch/plunger type device.

A solution of Potassium Hydroxide (KOH) was dispensed into each extraction tube containing the magnetically-responsive particles. The high pH KOH solution was dispensed by an automated robotic device, namely the BD Viper™ automated extractor device.

Urine samples were then dispensed into the extraction tubes, also by the automated robotic device. The urine samples are spiked to a level of 250 CT Ebs-250 GC parts/ml, and mixed with a high pH solution to lyse the organism(s) of interest contained in the sample, thereby releasing nucleic acid. A second solution with a low pH was added to the sample that binds the released nucleic acid to the magnetically-responsive particles. This solution contained Sulfuric Acid.

A magnetic field was applied to the contents of the extraction tube. The automated robotic device brought a pair of opposing magnets into close proximity with the outside of the tube, thereby drawing the complex to the inner periphery of the tube. The automated robotic device then aspirated the contents of the tube, leaving the complex therein, and the magnetic field was removed from the container.

The complex was then washed with a 1 mM concentration solution containing 0.01% Tween® 20. After washing, the magnetic field was reapplied to draw the complex to the inner periphery of the tube, and the wash was aspirated out of the tube.

An elution buffer solution was then added to the extraction tube, and mixed, to elute the nucleic acid from the complex. The elution buffer solution comprised a mixture based on a combination of KOH and Bicine. The elution buffer was added and mixed by the automated robotic device. The eluted sample nucleic acid was then separated and subjected to the following strand displacement amplification process (SDA).

An analyte-specific binding moiety was linked to the oligonucleotide moiety and mixed with the elution buffer mentioned above. The elution buffer containing the target was added to the priming microwells containing SDA primers CTpB4.S2.3, CTpB4.S1.3, or GCINT3.APR1, GCINT3.APL2, adapters ICAdpt.10, GCINT3.R2, or CTAdpt-F5, bumpers GCINT3.BR3, GCINT3.BL2, or CTpB4.B6, CTpB4.B7 and reporter probes MPC-DR, MPC3.FD, or MPC-FD. After 20 minutes at room temperature the mixture was then heated to 72-73° C. for 10 minutes. 100 µl of the mixture was then added to a 53.5-54.5° C. amplification wells. Specifically, commercially available BDProbeTec™ amplification wells were used.

BsoB1 restriction endonuclease and Bst DNA polymerase were added to the amplification wells and isothermal amplification was carried out for 60 minutes at 51.2-52.80° C. The amplification process was monitored with a BDProbeTec™ reader, which detected the fluorescent increase associated with reporter probe conversion. The reader produces MOTA (Measure Other Than Acceleration) values based on the detection of the above-described fluorescence during the amplification process. The MOTA values generated for the above-described samples are reported below in Table I and Table II.

TABLE I

CT Assay With Dissolvable Film

| Tube | Average MOTA Value |
|---|---|
| Control | 41,643 |
| Listerine Cool Mint ® | 30,740 |
| Listerine Fresh Burst ® | 27,190 |
| Listerine Cinnamon ® | 26,020 |
| Dissolvable film loaded with iron oxide | 28,605 |

TABLE II

GC Assay With Dissolvable Film

| Tube | Average MOTA Value |
|---|---|
| Control | 21,442 |
| Listerine Cool Mint ® | 22,242 |
| Listerine Fresh Burst ® | 32,318 |
| Listerine Cinnamon ® | 24,199 |
| Dissolvable film loaded with iron oxide | 28,818 |

For the above-reported assay, MOTA values greater than 2,000 are considered indicative of a positive result for the CT or GC target. With these criteria in mind, the above-reported data indicates that inclusion of the dissolvable film in the process did not significantly inhibit the extraction or amplification of the target sequence in obtaining a positive indication of the presence of the target during the assay.

EXAMPLE 2

An experiment was performed to determine the feasibility of incorporating a dissolvable film into a process of amplifying and detecting a RNA target, namely a SARS Co-V target sequence, as described below.

A SARS Co-V positive control tube was used as the target for the RT-SDA assay. The SARS Co-V positive control tube contained SAR Co-V Positive Control RNA Transcript, yeast RNA, and RNase Inhibitor. A negative SARS Co-V control was also used containing yeast RNA and RNase Inhibitor. Each SARS Co-V control tube was rehydrated with 950 µl of nuclease-free water and vortexed.

A working stock RT buffer was prepared by mixing the primary constituents nuclease-free water, RNase inhibitor, SARS Co-V internal amplification control, reverse transcriptase, KOH and Bicine.

The dissolvable film utilized in this experiment was clear carboxymethyl cellulose (without iron oxide). The film was cut into segments of varying sizes and placed into the SARS Co-V RT priming microwells containing nucleotides dCsTP, dATP, dGTP, dTTP, SDA primers SARSrpC, SARfpC, adapters SARSiacadC, SARSmpcadC, bumper SARSCrtB24, and reporter probes MPC-DR and MPC2.FD.

Positive or negative control and the working stock RT buffer were added to each of the respective SARS Co-V RT Priming microwells. After the SARS Co-V RT Priming microwells were heated to 48° C. for 20 minutes a second buffer primarily composed of Bicine and KOH was added to each reaction. The SARS Co-V RT Priming microwells were then heated to 72-73° C. for 10 minutes. 100 µl of the mixture was then added to a 53.5-54.5° C. amplification wells.

BsoB1 restriction endonuclease and Bst DNA polymerase were added to the amplification wells and isothermal amplification was carried out for 60 minutes at 51.2-52.8° C. The amplification process was monitored with a BDProbeTec™ reader, which detected the fluorescent increase associated with reporter probe conversion. The reader produces MOTA values based on the detection of the above-described reference values during the amplification process. These values are measured starting 3-7 minutes subsequent to the beginning of the amplification. The MOTA values generated for the above-described samples are reported below in Table III.

TABLE III

RT-SDA Reaction With Dissolvable Film

| Dissolvable Film Size | Average MOTA Value |
|---|---|
| None (Control) | 64447 |
| 3 × 3 mm | 77269 |
| 4 × 4 mm | 63519 |
| 5 × 5 mm | 68779 |

The above reported data indicates that the inclusion of the dissolvable film in the RT-SDA reaction did not inhibit the reverse transcription of RNA to DNA or the amplification of the target sequence in obtaining a positive indication of the presence of the target during the assay.

EXAMPLE 3

An experiment was performed to determine the feasibility of inclusion of a dissolvable film into a PCR amplification procedure, performed as described below. A plasmid construct pUC19-T. vaginalis was used as the template for the PCR process.

The film utilized in the experiments was carboxymethyl cellulose. The film was cut into segments of varying sizes and then placed into PCR thermowell tubes, and labeled as set forth below.

An array of PCR tubes were set up to perform the following reactions set forth in Table IV.

TABLE IV

PCR Reaction Set-Up

| Reaction Tube | Sample |
|---|---|
| 1 | PCR positive control (TV1) (no film) |
| 2 | PCR negative control (no TV1) (no film) |
| 3 | Film negative control (no TV1) (2 × 4 mm) |
| 4 | Film test PCR 1 (2 × 3 mm) (TV1) |
| 5 | Film test PCR 2 (2 × 4 mm) (TV1) |
| 6 | Film test PCR 3 (2 × 6 mm) (TV1) |
| 7 | Film test PCR 4 (2 × 10 mm) (TV1) |
| 8 | Film test PCR 5 (3 × 10 mm)(TV1) |

A 1×PCR reaction solution was prepared for addition to each of the tubes. The solution was prepared according to the composition of Table V.

TABLE V

PCR Reaction Solution Composition

| Constituent | Amount | Concentration | Source |
|---|---|---|---|
| T. vaginalis (TV1) | 11.2 μL | 89 ng/μL | Becton Dickinson |
| Pfu buffer | 100 μL | 10x | Stratagene |
| DNTP | 20 μL | 10 mM | Stratagene |
| TV1 (primer - 1) | 10 μL | 10 μM | IDT |
| TV2 (primer - 2) | 10 μL | 10 μM | IDT |
| Pfu enzyme (cloned) | 10 μL | 2.5 U/μL | Stratagene |
| Water | 838.8 μL | n/a | Becton Dickinson |
| TOTAL = | 1000 μL | | |

A 98.88 μL aliquot of the 1× solution was introduced into each of the 8 reaction tubes. A 1.12 μL charge of TV1 was added to tubes 1, 4, 5, 6, 7 and 8, and 1.12 μL of water was added to each of tubes 2 and 3. The tubes were then placed into a MJ Research Peltier Thermal Cycler (model PTC-200) and incubated under the conditions detailed in Table VI:

TABLE VI

Incubation Conditions

| Step | Temperature | Time | Cycles |
|---|---|---|---|
| 1 | 95° C. | 5 min | 1 |
| 2 | 95° C. | 45 sec | 35 |
| 3 | 52° C. | 45 sec | 35 |
| 4 | 72° C. | 90 sec | 35 |
| 5 | 72° C. | 10 min | 35 |
| 6 | 4° C. | indefinite | n/a |

A gel analysis of the PCR reaction product was then performed to gauge the results of the PCR amplification process. In this regard, a 1% agarose gel was prepared. Ethidium bromide was added to a final concentration of 0.5 μg/mL (10 μg if the 5 mg/mL stock into 100 mL of agarose mixture). A 40 ml amount of gel was poured and ran at 90V for 1 hour in 1×TBE according to the schedule set forth in Table VII.

TABLE VII

PCR Gel Set-Up

| Lane | Sample | Comments |
|---|---|---|
| 1 | Hyperladder | 5 μL hyperladder |
| 2 | PCR positive control (TV1) | 10 μL PCR + 1 μL 10x loading dye |
| 3 | PCR negative control (no TV1) | 10 μL PCR + 1 μL 10x loading dye |
| 4 | Film negative control (no TV1)(2 × 4 mm) | 10 μL PCR + 1 μL 10x loading dye |
| 5 | Film test PCR 1 (TV1) (2 × 3 mm) | 10 μL PCR + 1 μL 10x loading dye |
| 6 | Film test PCR 2 (TV1) (2 × 4 mm) | 10 μL PCR + 1 μL 10x loading dye |
| 7 | Film test PCR 3 (TV1) (2 × 6 mm) | 10 μL PCR + 1 μL 10x loading dye |
| 8 | Film test PCR 4 (TV1) (2 × 10 mm) | 10 μL PCR + 1 μL 10x loading dye |
| 9 | Film test PCR 5 (TV1) (3 × 10 mm) | 10 μL PCR + 1 μL 10x loading dye |
| 10 | Film test PCR 6 (TV1) (2 × 9 mm) | 10 μL PCR + 1 μL 10x loading dye |
| 11 | Empty | |
| 12 | Hyperladder | 5 μL hyperladder |

Figure 4:
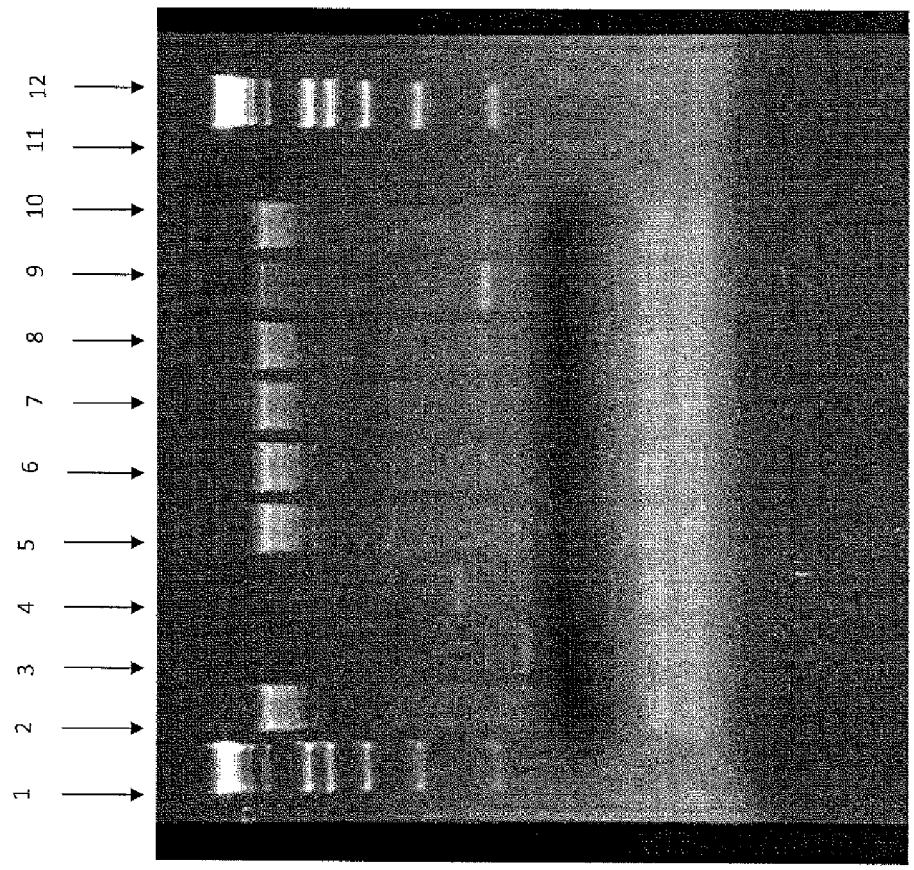
FIG. 4 is an image of the results of a PCR procedure performed according to one aspect of the present invention.

The results of the gel run are illustrated in FIG. 4, and indicate a successful PCR procedure, thereby indicating that the presence of the dissolvable film did not act as an inhibitor or otherwise disrupt the PCR procedure. As indicated in FIG. 4, the presence of dissolvable film of a size of up to 30 mm$^2$ does not inhibit the PCR process.

EXAMPLE 4

An experiment was performed to determine the feasibility of incorporating a dissolvable film into a process of amplifying and detecting a DNA target, namely a *Chlamydia trachomatis* (CT) or *Neisseria gonorrhoeae* (GC) target sequences, as described below.

A CT/GC positive control tube was used as the target for the CT/GC Diplex SDA assays. The CT/GC positive control tube contained CT/GC positive control plasmid, salmon sperm DNA, and control dry down diluent. A negative CT/GC control was also used containing salmon sperm DNA, and control dry down diluent. Each CT/GC control tube was rehydrated with 2 ml of sample diluent and vortexed.

All control tubes were heat lysed at 114° C. for 30 minutes. Each control tube was then allowed to cool down for at least 15 minutes prior to testing.

The dissolvable film utilized in this experiment was clear carboxymethyl cellulose (without iron oxide). The film was cut into segments of varying sizes and placed into the CT/GC priming microwells containing SDA primers CTpB4.S2.3, CTpB4.S1.3, or GCINT3.APR1, GCINT3.APL2, adapters ICAdpt.10, GCINT3.R2, or CTAdpt-F5, bumpers GCINT3.BR3, GCINT3.BL2, CTpB4.B or CTpB4.B7 and reporter probes MPC-DR, MPC3.FD, or MPC-FD.

Positive or negative controls were added to each of the respective CT/GC priming microwells. The CT/GC priming microwells were then heated to 72-73° C. for 10 minutes. 100 μl of the mixture was then added to a 53.5-54.5° C. CT/GC amplification microwells.

The amplification microwells were then added to BD ProbeTec™ model 1334 reader where an isothermal amplification was carried out for 60 minutes at 51.2-52.8° C. The amplification process was monitored by observing the fluorescence increase associated with conversion of the reporter probed. The reader produces MOTA values based on the detection of the above-described reference values during the amplification process. These values are measured starting 3-7 minutes subsequent to the beginning of the amplification. The MOTA values generated for the above-described samples are reported below in Table VIII (CT) and Table IX (GC).

TABLE VIII

MOTA Values For CT Samples

| | CT | | | | | | | |
|---|---|---|---|---|---|---|---|---|
| | Negative Control | | | | Positive Control | | | |
| | No Film (Control) | 3 × 3 mm | 4 × 4 mm | 5 × 5 mm | No Film (Control) | 3 × 3 mm | 4 × 4 mm | 5 × 5 mm |
| | 500 | 830 | 0 | 500 | 54860 | 70590 | 62530 | 48860 |
| | 950 | 370 | 0 | 0 | 58520 | 68010 | 69850 | 59460 |
| | 300 | 440 | 0 | 0 | 55840 | 63250 | 76160 | 78750 |
| Average: | 583 | 547 | 0 | 167 | 56407 | 67283 | 69513 | 62357 |
| STDEV: | 333 | 248 | 0 | 289 | 1895 | 3724 | 6821 | 15154 |

TABLE IX

MOTA Values For GC Samples

| | GC | | | | | | | |
|---|---|---|---|---|---|---|---|---|
| | Negative Control | | | | Positive Control | | | |
| | No Film (Control) | 3 × 3 mm | 4 × 4 mm | 5 × 5 mm | No Film (Control) | 3 × 3 mm | 4 × 4 mm | 5 × 5 mm |
| | 160 | 0 | 0 | 0 | 17680 | 23230 | 18210 | 40750 |
| | 370 | 0 | 0 | 0 | 26360 | 30270 | 22130 | 59710 |
| | 70 | 0 | 0 | 0 | 20090 | 30810 | 30470 | 43560 |
| Average: | 200 | 0 | 0 | 0 | 21377 | 28103 | 23603 | 48007 |
| STDEV: | 154 | 0 | 0 | 0 | 4481 | 4229 | 6261 | 10232 |

The data shown above illustrates the feasibility of utilizing dissolvable film directly in a Diplex SDA reaction. Insertion of the film directly into the SDA amplification microwells does not inhibit the reaction.

EXAMPLE 5

An experiment was performed to determine if the dissolvable film would interfere with the extraction procedure. An extraction control (EC) is a labeled oligonucleotide included with the extraction mixture. The fluorescence of the label is monitored to determine if the extraction process is successful. Two dissolvable films (containing iron oxide) and two types of iron oxide particles were tested to determine their effect, if any, on the extraction process.

Containers in the form of extraction tubes were provided with magnetically-responsive particles according to the following techniques: (1) Approximately 9 mg iron particles (particle sample A or particle sample B) dispensed into the extraction tube; or (2) A dissolvable film (film sample A or film sample B) loaded with iron particles at a concentration of 9.9 mg/1.77 cm$^2$. Positive control tubes included the fluorescently-labeled extraction control oligonucleotide, while the negative controls contained no extraction control. The remainder of the extraction process was completed as described in Example 1. The fluorescence of the labeled EC oligonucleotide was then measured to determine if extraction was successful. No amplification steps were performed on the samples.

The results of the extraction are shown in Tables X (CT) and XI (GC). These tables illustrate an EC metric which utilizes a 0.5 value for positive results. Values below 0.5 are considered a negative result.

TABLE X

Effect of Iron Particles on CT Extraction Process
CT ASSAY

| | Sample Film A | | Sample Powder A | | Sample Film B | | Sample Powder B | |
|---|---|---|---|---|---|---|---|---|
| | w/EC | w/out EC | w/EC | w/out EC | w/EC | w/out EC | w/EC | w/out EC |
| | 0.7 | 0.2 | 0.7 | 0.2 | 0.7 | 0.3 | 0.7 | 0.2 |
| | 0.6 | 0.2 | 0.8 | 0.2 | 0.8 | 0.2 | 0.8 | 0.2 |
| | 0.7 | 0.3 | 0.7 | 0.2 | 0.7 | 0.2 | 0.7 | 0.2 |
| | 0.8 | 0.3 | 0.7 | 0.2 | 0.7 | 0.3 | 0.7 | 0.2 |
| | 0.8 | 0.2 | 0.8 | 0.2 | 0.8 | 0.2 | 0.7 | 0.2 |
| | 0.8 | 0.2 | 0.7 | 0.2 | 0.6 | 0.2 | 0.8 | 0.2 |
| | 0.9 | 0.2 | 0.8 | 0.2 | 0.7 | 0.3 | 0.7 | 0.2 |
| | 0.9 | 0.2 | 0.7 | 0.2 | 0.6 | 0.3 | 0.7 | 0.2 |
| | 0.6 | 0.2 | 0.7 | 0.2 | 0.8 | 0.2 | 0.7 | 0.2 |
| | 0.8 | 0.2 | 0.7 | 0.2 | 0.8 | 0.3 | 0.9 | 0.2 |
| | 0.7 | 0.2 | 0.7 | 0.2 | 0.8 | 0.2 | 0.7 | 0.2 |
| | 0.7 | 0.2 | 0.7 | 0.2 | 0.9 | 0.2 | 0.7 | 0.2 |
| Average: | 0.8 | 0.2 | 0.7 | 0.2 | 0.7 | 0.2 | 0.7 | 0.2 |

TABLE XI

Effect of Iron Particles on GC Extraction Process
GC ASSAY

| | Sample Film A | | Sample Powder A | | Sample Film B | | Sample Powder B | |
|---|---|---|---|---|---|---|---|---|
| | w/EC | w/out EC | w/EC | w/out EC | w/EC | w/out EC | w/EC | w/out EC |
| | 0.6 | 0.2 | 0.7 | 0.2 | 0.9 | 0.3 | 0.7 | 0.2 |
| | 0.7 | 0.2 | 0.6 | 0.2 | 0.8 | 0.2 | 0.8 | 0.2 |
| | 0.7 | 0.3 | 0.7 | 0.2 | 0.7 | 0.3 | 0.7 | 0.2 |
| | 0.8 | 0.3 | 0.7 | 0.2 | 0.7 | 0.3 | 0.7 | 0.2 |
| | 0.8 | 0.3 | 0.9 | 0.2 | 0.8 | 0.3 | 0.8 | 0.2 |

TABLE XI-continued

Effect of Iron Particles on GC Extraction Process
GC ASSAY

|  | Sample Film A | | Sample Powder A | | Sample Film B | | Sample Powder B | |
|---|---|---|---|---|---|---|---|---|
|  | w/EC | w/out EC | w/EC | w/out EC | w/EC | w/out EC | w/EC | w/out EC |
|  | 0.9 | 0.2 | 0.8 | 0.2 | 0.6 | 0.2 | 1.0 | 0.3 |
|  | 0.8 | 0.3 | 0.9 | 0.2 | 0.7 | 0.3 | 0.7 | 0.3 |
|  | 0.9 | 0.3 | 0.9 | 0.2 | 0.6 | 0.3 | 0.9 | 0.2 |
|  | 0.7 | 0.3 | 0.8 | 0.2 | 0.8 | 0.3 | 0.8 | 0.2 |
|  | 0.8 | 0.3 | 0.9 | 0.2 | 0.9 | 0.2 | 0.9 | 0.2 |
|  | 0.8 | 0.3 | 0.7 | 0.2 | 0.8 | 0.3 | 0.8 | 0.2 |
|  | 0.8 | 0.2 | 0.9 | 0.2 | 1.0 | 0.2 | 0.7 | 0.2 |
| Average: | 0.8 | 0.3 | 0.8 | 0.2 | 0.8 | 0.3 | 0.8 | 0.2 |

The data illustrates no adverse effect on the ability to extract the Extraction Control with the incorporation of iron particles, either embedded in dissolvable film or as free iron particles. The positive average values recorded for all dissolvable film samples (0.7 and 0.8) indicate a successful extraction process.

EXAMPLE 6

An experiment was performed to determine the feasibility of incorporating the dissolvable film into a process of detecting a target analyte in different types of samples. In particular, an assay for CT or GC was performed as described below. An analysis of the effects of the dissolvable film was made.

Four types of samples were used in the present assay: Urine, Sample Diluent, Clinical Urine and Vaginal Swabs. A "Urine" sample is an in-house sample pool collected from healthy donors. "Sample Diluent" refers to a current BD ProbeTec™ sample buffer that is used to rehydrate control tubes as well as the matrix into which swabs are expressed. "Clinical Urine" refers to urine specimens obtained from people who have been diagnoses with a condition or illness. The extraction tubes were provided with magnetically-responsive particles in the form of one of two types of dissolvable films (Sample Film A and Sample Film B) loaded with iron oxide particles at concentrations of 9.7 mg/1.77 cm$^2$ and 10.6 mg/cm$^2$, respectively. The samples were extracted and amplified as described in Example 1. The MOTA values generated for the above-described samples are reported below in Tables XII and XIII.

TABLE XII

Evaluation of CT Assay In Different Sample Types
CT ASSAY

| Sample Matrix: | | | | | | | | |
|---|---|---|---|---|---|---|---|---|
| Sample Diluent | | Clinical Urine | | Urine | | Vaginal Swabs | | |
| Sample Film Type: | | | | | | | | |
| A | B | A | B | A | B | A | B |
| 37040 | 20060 | 16410 | 23450 | 20240 | 41760 | 41110 | 25800 |
| 9010 | 17170 | 31540 | 9350 | 15020 | 21860 | 50930 | 29370 |
| 25110 | 25180 | 13760 | 24860 | 34290 | 19750 | 41340 | 68720 |
| 11570 | 29080 | 41780 | 16900 | 18920 | 21380 | 46100 | 28210 |
| 18860 | 10380 | 43450 | 26910 | 13680 | 28000 | 47110 | 23030 |
| 27610 | 22440 | 15500 | 33470 | 11930 | 9320 | 64920 | 25010 |
| 15040 | 21410 | 15660 | 11530 | 14780 | 36460 | 17160 | 18500 |
| 28580 | 18650 | 20940 | 31230 | 17920 | 20200 | 23730 | 37400 |
| 19590 | 35620 | 61010 | 61900 | 39110 | 21010 | 29230 | 50110 |
| 9890 | 15320 | 10770 | 13450 | 11030 | 18690 | 32130 | 29460 |
| 23970 | 10210 | 16710 | 14460 | 32700 | 29110 | 22800 | 16320 |
| 11990 | 12890 | 31600 | 32300 | 16800 | 9940 | 51360 | 30030 |
| Average: 19855 | 19868 | 26594 | 24984 | 20535 | 23123 | 38993 | 31830 |

TABLE XIII

Evaluation of GC Assay In Different Sample Types
GC ASSAY

| Sample Matrix: | | | | | | | | |
|---|---|---|---|---|---|---|---|---|
| Sample Diluent | | Clinical Urine | | Urine | | Vaginal Swabs | | |
| Sample Film Type: | | | | | | | | |
| A | B | A | B | A | B | A | B |
| 15020 | 28380 | 18860 | 14510 | 24650 | 15710 | 14610 | 11420 |
| 12130 | 13440 | 16240 | 9720 | 17760 | 37330 | 29670 | 14460 |
| 15650 | 11260 | 9600 | 15460 | 22280 | 30170 | 13870 | 21400 |
| 19440 | 16920 | 24540 | 15540 | 19640 | 47410 | 9020 | 15600 |
| 22420 | 15470 | 35040 | 25600 | 27810 | 28570 | 7820 | 10040 |
| 12540 | 18220 | 40590 | 24420 | 22540 | 34940 | 14170 | 13310 |
| 28360 | 30320 | 17860 | 23140 | 58940 | 20230 | 13670 | 20250 |
| 17260 | 12160 | 20960 | 15690 | 32060 | 16390 | 18480 | 24100 |

TABLE XIII-continued

Evaluation of GC Assay In Different Sample Types
GC ASSAY

| | Sample Matrix: | | | | | | | |
|---|---|---|---|---|---|---|---|---|
| | Sample Diluent | | Clinical Urine | | Urine | | Vaginal Swabs | |
| | Sample Film Type: | | | | | | | |
| | A | B | A | B | A | B | A | B |
| | 22000 | 15580 | 13750 | 9170 | 17060 | 20170 | 10620 | 18990 |
| | 17380 | 10640 | 29850 | 9780 | 10480 | 13230 | 9720 | 16590 |
| | 15220 | 15920 | 17190 | 13580 | 11090 | 26180 | 12850 | 16210 |
| | 17570 | 12450 | 15140 | 36990 | 11040 | 16110 | 11600 | 27910 |
| Average: | 17916 | 16730 | 21635 | 17800 | 22946 | 25537 | 13842 | 17523 |

The above data shows that inclusion of either type of dissolvable film did not significantly inhibit the extraction or amplification of the target sequence in any of the four sample types.

EXAMPLE 7

An experiment was performed to determine if the magnetically-responsive particles, in the form of iron powder or dissolvable film, would interfere in the process of detecting a target analyte. The experiment evaluated the effect of the dissolvable film in both a SDA monoplex and diplex system. In particular, an assay for CT utilizing Sample Diluent and Urine Pool samples were performed as described below.

In a monoplex assay, a universal detector probe is utilized for real-time fluorescence energy transfer detection of a target. A diplex assay utilizes an internal amplification control (IAC) in addition to the detector probe. The IAC is co-amplified with the target DNA to identify samples that may contain inhibitors of the SDA reaction.

In the present Example, the extraction tubes were provided with iron particles in the form of free iron powder or a dissolvable film loaded with iron particles at a concentration of approximately 9.0 mg/1.77 $cm^2$. The samples were extracted and amplified as described previously in Example 1. Results are shown in Tables XIV and XV. The Tables show "PAT" values. "PAT" refers to Passes After Threshold, an algorithm used in determining positive samples. A signal is timed to a predetermined threshold value, which is then subtracted by the number of passes the BD ProbeTec™ performs. A higher final PAT value indicates the sample reached the threshold resulting in a positive result at a faster rate than a sample with a lower value. A PAT equal to zero is considered negative. Therefore, values above zero indicate positive results.

TABLE XIV

CT Monoplex and Diplex Assay With Sample Diluent
Sample Diluent

| | Diplex Assay | | Monoplex Assay | |
|---|---|---|---|---|
| | Film | Powder | Film | Powder |
| | 43.91 | 43.41 | 50.84 | 52.58 |
| | 47.35 | 43.41 | 51.95 | 52.35 |
| | 44.76 | 43.91 | 51.65 | 52.43 |
| | 48.22 | 45 | 52.46 | 52.49 |
| | 46.18 | 43.48 | 52.28 | 52.5 |
| | 47.59 | 44.03 | 52.34 | 52.12 |
| | 45.08 | 45.63 | 52.49 | 52.5 |
| | 45.89 | 44.52 | 52.29 | 51.41 |

TABLE XIV-continued

CT Monoplex and Diplex Assay With Sample Diluent
Sample Diluent

| | Diplex Assay | | Monoplex Assay | |
|---|---|---|---|---|
| | Film | Powder | Film | Powder |
| | 44.36 | 48.2 | 52.24 | 52.11 |
| | 46.67 | 47.76 | 52.35 | 52.22 |
| | 46.22 | 47.7 | 52.2 | 52.33 |
| | 44.7 | 47.27 | 52.22 | 52.15 |
| Average: | 46 | 45 | 52 | 52 |

TABLE XV

CT Monoplex and Diplex Assay With Urine Pool
Urine Pool

| | Diplex Assay | | Monoplex Assay | |
|---|---|---|---|---|
| | Film | Powder | Film | Powder |
| | 43.32 | 45.47 | 52.37 | 52.1 |
| | 42.55 | 45.9 | 52.07 | 52.26 |
| | 45.83 | 45.63 | 52.09 | 52.31 |
| | 45.6 | 46.55 | 52.4 | 52.44 |
| | 46.97 | 46.23 | 52.55 | 52.29 |
| | 44.09 | 45.97 | 52.36 | 52.36 |
| | 46.34 | 46.29 | 52.37 | 52.39 |
| | 46.03 | 44.95 | 52.35 | 52.32 |
| | 46.3 | 47.72 | 52.51 | 52.21 |
| | 45.38 | 44.1 | 52.44 | 51.97 |
| | 46.41 | 48.01 | 52.02 | 51.97 |
| | 44.88 | 43.64 | 51.38 | 52.18 |
| Average | 45 | 46 | 52 | 52 |

The data displayed in Tables XIV and XV illustrate that the dissolvable film performed as well as the free iron powder in both the monoplex and diplex assays. The positive PAT values indicate successful amplification of the target in both assays.

EXAMPLE 8

An experiment was performed to determine the optimum mixing parameters for the BD Viper™ automated extractor device to insure dissolution of the dissolvable film with the incorporated iron oxide. This allows the target DNA ample time to be bound and captured by the iron particles. This experiment evaluated multiple mixing parameters on the BD Viper™ instrument.

The extraction procedures for the present experiment are the same as those described in Example 1 with the modifications described below. Eight different sample conditions were tested, as described in Table XVI. Six duplicate tubes were prepared for each condition. The extraction tubes were provided with dissolvable film containing iron particles at a concentration of 9.8 mg/1.77 cm². The Sample Diluent was then added to the extraction tubes and mixed at a specified volumes and speeds. This experiment was run to eliminate a twenty-second pause in the current BD Viper™ program. The control extraction tubes were exposed to KOH and mixed 5 times. The tubes were then incubated for 20 seconds to allow dissolution. This incubation was followed by one mixing step with a binding acid mixture containing 3.75M sulfuric acid and an extraction control. In the subsequent test conditions the KOH mix and dissolution pause was removed. The mixing speed and number of mixing repetitions were also varied as indicated in Table XVI. The color of the fluid within the sample tips of the BD Viper™ instrument was visually noted. The iron oxide powder is black and the sample diluent clear. Therefore, an acceptable mixing result was achieved when the fluid in the sample tip was completely black, indicating complete mixing. The resulting color in the tips was rated as follows: (0)=Poor; (1)=Fair; (2)=Good; (3)=Very Good.

TABLE XVI

Optimization Of Mixing Parameters

| Sample # | Test Conditions: | Mixing Speed | Mixing Volume | # of Mixes | Time For Step | Results |
|---|---|---|---|---|---|---|
| 1 | 1st Acid + EC Mix | 50% | 438 ul (50%) | 10 | 27 sec. | 0 |
|   | 2nd Acid + EC Mix | 80% | 700 ul | 5 | 17 sec. |   |
| 2 | 1st Acid + EC Mix | 80% | 612 ul (70%) | 10 | 27 sec. | 0 |
|   | 2nd Acid + EC Mix | 50% | 700 ul | 5 | 17 sec. |   |
| 3 | 1st Acid + EC Mix | 80% | 612 ul (70%) | 10 | 27 sec. | 2 |
|   | 2nd Acid + EC Mix | 80% | 700 ul | 10 | 30 sec. |   |
| 4 | 1st Acid + EC Mix | 80% | 612 ul (70%) | 5 | 14 sec. | 0 |
|   | 2nd Acid + EC Mix | 50% | 700 ul | 10 | 34 sec. |   |
| 5 | 1st Acid + EC Mix | 50% | 612 ul (70%) | 5 | 14 sec. | 1 |
|   | 2nd Acid + EC Mix | 80% | 700 ul | 10 | 30 sec. |   |
| 6 | 1st Acid + EC Mix | 50% | 612 ul (70%) | 10 | 27 sec. | 2 |
|   | 2nd Acid + EC Mix | 80% | 700 ul | 10 | 30 sec. |   |
| 7 | 1st Acid + EC Mix | 80% | 438 ul (50%) | 10 | 27 sec. | 2 |
|   | 2nd Acid + EC Mix | 80% | 700 ul | 10 | 30 sec. |   |
| 8 | 1st Acid + EC Mix | 80% | 438 ul (50%) | 15 | 33 sec. | 3 |
|   | 2nd Acid + EC Mix | 80% | 700 ul | 10 | 30 sec. |   |

The above experiment determined that condition #8 (438 μl mixing volume for 15 mixes followed by 700 μl mixing volume for 10 mixes) was ideal for the complete dissolution of the dissolvable film. This condition provided a result of "Very Good" upon visual inspection.

EXAMPLE 9

An experiment was performed to test the optimized parameters described in Experiment 8. Specifically, a CT assay was performed as described below.

Extraction tubes were provided with magnetically-responsive particles in the form of either iron powder (Sample Powder A or Sample Powder B) or a dissolvable film loaded with iron particles. Vaginal swab samples were added to the extraction tubes. The samples were mixed as outlined in Experiment 8 (438 μl mixing volume for 15 mixes followed by 700 μl mixing volume for 10 mixes) and amplified as described in Experiment 1. Results are illustrated in Table XVII and expressed as PAT scores.

TABLE XVII

CT Assay Utilizing Optimized Mixing Parameters
CT ASSAY

| Dissolvable Film | | Sample Powder A | | Sample Powder B | |
|---|---|---|---|---|---|
| Target | IAC | Target | IAC | Target | IAC |
| 43.40 | 51.50 | 38.30 | 50.40 | 42.50 | 52.30 |
| 49.60 | 42.20 | 45.90 | 44.50 | 49.60 | 44.00 |
| 43.60 | 50.70 | 45.20 | 46.50 | 48.30 | 45.30 |
| 45.30 | 48.80 | 47.30 | 41.60 | 42.90 | 50.80 |
| 48.70 | 39.90 | 44.70 | 27.90 | 46.30 | 45.30 |
| 45.50 | 49.20 | 45.70 | 45.90 | 45.60 | 48.20 |
| 43.50 | 47.20 | 43.30 | 42.20 | 40.80 | 48.90 |
| 45.10 | 46.10 | 44.10 | 45.40 | 44.50 | 50.30 |
| 43.20 | 49.70 | 39.80 | 48.90 | 46.40 | 46.80 |
| 46.10 | 46.90 | 44.30 | 46.10 | 47.80 | 31.60 |
| 37.40 | 49.90 | 32.70 | 48.90 | 44.80 | 44.60 |
| 39.70 | 46.40 | 46.60 | 49.00 | 44.40 | 48.10 |
| 45.00 | 40.40 | 44.60 | 12.80 | 46.20 | 35.90 |
| 42.30 | 45.50 | 44.00 | 46.70 | 43.20 | 36.50 |
| 43.60 | 45.20 | 42.90 | 25.70 | 37.00 | 44.70 |
| 41.70 | 41.10 | 42.90 | 42.00 | 42.80 | 45.10 |
| Average: 44.0 | 46.3 | 43.3 | 41.5 | 44.6 | 44.9 |

The above data illustrates that the optimized mixing parameters determined in Experiment 8 result in successful extraction and amplification reactions as indicated by the positive (>0) PAT scores for both the target and IAC.

EXAMPLE 10

An experiment was performed to test the stability of the dissolvable film over one month at varying temperatures. The film was stored at one of three consistent temperature ranges (2-8° C., 15° C. and 33° C.) for one month. The reagents were removed from storage and tested in extraction/amplification reactions at ambient temperatures. Tables XVIII through XXIII show the results of the CT and GC assays performed on the reagents stored at each temperature range. The experiments were conducted as previously described in Example 1. Positive (Target) Values measure amplified CT target. Negative (IAC) Values measure Internal Amplification Control fluorescence. Data is recorded as PAT scores.

TABLE XVIII

CT Assay Testing On Film Stored at 2-8° C.
2-8° C. Reagent Storage Condition
CT ASSAY

| Positive (Target) Values | | | | Negative (IAC) Values | | | |
|---|---|---|---|---|---|---|---|
| 48.90 | 50.30 | 49.80 | 47.50 | 44.60 | 48.20 | 48.80 | 49.60 |
| 49.20 | 50.30 | 48.90 | 49.40 | 46.20 | 48.30 | 49.00 | 49.70 |
| 49.20 | 50.50 | 46.00 | 47.40 | 46.30 | 48.30 | 49.00 | 49.80 |
| 50.20 | 48.40 | 48.30 | 49.00 | 46.30 | 48.40 | 49.10 | 49.80 |
| 49.40 | 47.30 | 49.40 | 49.10 | 46.50 | 48.50 | 49.10 | 49.90 |
| 50.30 | 49.50 | 48.90 | 48.40 | 46.50 | 48.60 | 49.30 | 50.00 |
| 49.80 | 48.70 | 48.70 | 49.00 | 46.90 | 48.70 | 49.30 | 50.10 |
| 49.10 | 49.00 | 44.90 | 49.20 | 47.00 | 48.70 | 49.30 | 50.20 |

TABLE XVIII-continued

CT Assay Testing On Film Stored at 2-8° C.
2-8° C. Reagent Storage Condition
CT ASSAY

| Positive (Target) Values | | | | Negative (IAC) Values | | | |
|---|---|---|---|---|---|---|---|
| 48.20 | 48.40 | 48.30 | 49.40 | 47.40 | 48.70 | 49.30 | 50.60 |
| 49.70 | 48.50 | 48.30 | 48.00 | 47.70 | 48.80 | 49.50 | 50.80 |
| 48.40 | 46.80 | 47.50 | 46.20 | 47.70 | 48.80 | 49.50 | 50.80 |
| 49.60 | 49.20 | 49.90 | 46.40 | 48.10 | 48.80 | 49.60 | *Empty |
| Average: | | 48.68 | | | | 48.64 | |

No False Positives observed
*The IAC dropout was result of a BD Viper ™ fluid level error.

TABLE XIX

GC Assay Testing On Film Stored at 2-8° C.
2-8° C. Reagent Storage Condition
GC ASSAY

| Positive (Target) Values | | | | Negative (IAC) Values | | | |
|---|---|---|---|---|---|---|---|
| 40.20 | 42.30 | 42.10 | 41.00 | 12.80 | 42.70 | 43.90 | 45.10 |
| 41.80 | 44.70 | 44.20 | 27.80 | 36.20 | 42.70 | 43.90 | 45.20 |
| 33.50 | 43.90 | 43.90 | 42.00 | 40.20 | 43.00 | 44.20 | 45.20 |
| 43.00 | 42.90 | 44.90 | 41.40 | 40.20 | 43.20 | 44.40 | 45.50 |
| 40.90 | 42.30 | 44.70 | 44.40 | 40.20 | 43.30 | 44.50 | 45.80 |
| 37.70 | 44.20 | 39.70 | 40.30 | 40.30 | 43.30 | 44.50 | 45.80 |
| 43.70 | 37.80 | 42.30 | 42.30 | 40.70 | 43.40 | 44.50 | 45.90 |
| 42.90 | 37.80 | 41.60 | 32.50 | 41.50 | 43.40 | 44.80 | 46.00 |
| 41.20 | 40.10 | 42.30 | 42.50 | 41.50 | 43.60 | 45.00 | 46.50 |
| 42.20 | 43.70 | 45.60 | 28.70 | 42.10 | 43.60 | 45.00 | 46.70 |
| 43.50 | 44.70 | 43.30 | 43.80 | 42.30 | 43.70 | 45.00 | 47.50 |
| 43.70 | 41.90 | 41.60 | 51.00 | 42.50 | 43.70 | 45.00 | *Empty |
| Average: | | 41.55 | | | | 42.98 | |

No False Positives observed
*The IAC dropout was result of a BD Viper ™ fluid level error.

TABLE XX

CT Assay Testing On Film Stored at 15° C.
15° C. Reagent Storage Condition
CT ASSAY

| Positive (Target) Values | | | | Negative (IAC) Values | | | |
|---|---|---|---|---|---|---|---|
| 50.00 | 50.80 | 50.50 | 48.20 | 43.60 | 47.50 | 48.50 | 49.70 |
| 50.50 | 50.20 | 49.30 | 49.80 | 44.10 | 47.80 | 48.50 | 49.70 |
| 49.00 | 50.40 | 47.60 | 48.90 | 45.90 | 47.90 | 48.60 | 49.70 |
| 50.50 | 50.20 | 48.20 | 48.30 | 45.90 | 48.10 | 48.60 | 49.90 |
| 49.30 | 50.80 | 48.00 | 45.60 | 45.90 | 48.10 | 48.80 | 50.00 |
| 50.30 | 48.60 | 47.40 | 45.10 | 46.30 | 48.10 | 48.90 | 50.10 |
| 48.50 | 49.10 | 48.00 | 47.50 | 46.50 | 48.20 | 49.00 | 50.20 |
| 49.70 | 46.20 | 48.70 | 49.60 | 46.70 | 48.30 | 49.10 | 50.20 |
| 49.40 | 50.30 | 49.50 | 47.50 | 46.80 | 48.30 | 49.10 | 50.40 |
| 48.60 | 50.20 | 49.00 | 47.30 | 46.90 | 48.40 | 49.30 | 50.50 |
| 49.90 | 49.40 | 49.00 | 46.80 | 47.10 | 48.40 | 49.30 | 51.10 |
| 49.70 | 50.40 | 45.90 | *Empty | 47.40 | 48.40 | 49.60 | 52.00 |
| Average: | | 47.87 | | | | 48.36 | |

*The positive dropouts are a result of a BD Viper ™ fluid level error.
No False Positives observed

TABLE XXI

GC Assay Testing On Film Stored at 15° C.
15° C. Reagent Storage Condition
GC ASSAY

| Positive (Target) Values | | | | Negative (IAC) Values | | | |
|---|---|---|---|---|---|---|---|
| 44.70 | 42.70 | 44.40 | 40.10 | 37.50 | 43.90 | 45.20 | 45.70 |
| 45.70 | 44.90 | 40.10 | 42.70 | 38.00 | 43.90 | 45.30 | 45.70 |
| 42.00 | 41.60 | 42.60 | 43.20 | 39.80 | 43.90 | 45.30 | 46.00 |
| 44.00 | 46.00 | 40.60 | 39.30 | 41.50 | 44.40 | 45.30 | 46.00 |
| 37.20 | 44.50 | 43.20 | 38.80 | 41.50 | 44.40 | 45.40 | 46.00 |
| 22.90 | 32.00 | 41.50 | 35.00 | 41.60 | 44.50 | 45.40 | 46.40 |
| 40.70 | 43.10 | 45.30 | 39.80 | 42.80 | 44.80 | 45.50 | 46.40 |
| 43.80 | 44.30 | 38.40 | 41.80 | 43.10 | 44.90 | 45.60 | 46.50 |
| 39.80 | 43.50 | 41.20 | 7.30 | 43.30 | 45.00 | 45.60 | 46.60 |
| 44.40 | 32.30 | 44.10 | 44.90 | 43.50 | 45.00 | 45.70 | 47.50 |
| 42.30 | 43.50 | 43.40 | 42.40 | 43.70 | 45.00 | 45.70 | 47.60 |
| 39.50 | 45.90 | 46.00 | *Empty | 43.90 | 45.10 | 45.70 | 49.10 |
| Average: | | 39.93 | | | | 44.59 | |

*The positive dropouts are a result of a BD Viper ™ fluid level error.
No False Positives observed

TABLE XXII

CT Assay Testing On Film Stored At 33° C.
33° C. Reagent Storage Condition
CT ASSAY

| Positive (Target) Values | | | | Negative (IAC) Values | | | |
|---|---|---|---|---|---|---|---|
| 50.40 | 46.50 | 42.60 | 48.90 | 44.70 | 47.70 | 48.70 | 49.40 |
| 49.50 | 48.30 | 50.40 | 48.90 | 45.20 | 47.70 | 48.70 | 49.50 |
| 49.90 | 50.10 | 49.60 | 50.20 | 45.20 | 47.80 | 48.80 | 49.60 |
| 50.80 | 51.50 | 48.70 | 49.70 | 45.50 | 48.10 | 48.80 | 49.80 |
| 49.90 | 47.30 | 47.60 | 47.50 | 46.20 | 48.10 | 48.80 | 49.90 |
| 51.60 | 49.50 | 50.10 | 48.20 | 46.30 | 48.20 | 48.90 | 49.90 |
| 50.50 | 50.90 | 51.20 | 48.40 | 46.50 | 48.20 | 48.90 | 50.10 |
| 50.00 | 50.70 | 48.90 | 49.30 | 47.00 | 48.60 | 48.90 | 50.30 |
| 50.10 | 50.90 | 49.80 | 49.30 | 47.00 | 48.60 | 49.00 | 50.40 |
| 50.60 | 50.00 | 49.20 | 49.30 | 47.10 | 48.60 | 49.10 | 50.60 |
| 51.40 | 48.70 | 50.50 | 48.90 | 47.30 | 48.60 | 49.10 | 50.60 |
| 50.90 | 49.70 | 49.40 | *Empty | 47.40 | 48.60 | 49.20 | 50.90 |
| Average: | | 48.46 | | | | 48.38 | |

*The positive dropouts are a result of a BD Viper ™ fluid level error.
No False Positives observed

TABLE XXIII

GT Assay Testing On Film Stored At 33° C.
33° C. Reagent Storage Condition
GC ASSAY

| Positive (Target) Values | | | | Negative (IAC) Values | | | |
|---|---|---|---|---|---|---|---|
| *Empty | 44.70 | 40.90 | 40.60 | 22.50 | 43.60 | 45.00 | 46.50 |
| 46.40 | 37.30 | 43.80 | 43.10 | 34.70 | 43.70 | 45.10 | 46.60 |
| 12.90 | 43.60 | 45.30 | 43.80 | 41.00 | 43.80 | 45.30 | 46.60 |
| 43.70 | 44.30 | 44.10 | 42.90 | 41.20 | 44.00 | 45.40 | 46.60 |
| 45.20 | 41.70 | 44.80 | 37.40 | 41.70 | 44.20 | 45.40 | 46.70 |
| 40.80 | 45.80 | 46.20 | 43.20 | 42.00 | 44.20 | 45.60 | 46.70 |
| 40.60 | 45.40 | 43.10 | 34.60 | 42.20 | 44.50 | 45.70 | 46.80 |
| 43.40 | 43.20 | 39.40 | 44.80 | 42.70 | 44.60 | 45.70 | 47.00 |
| 45.80 | 45.30 | 35.60 | 28.10 | 42.70 | 44.60 | 45.90 | 47.30 |
| 45.20 | 38.90 | 35.60 | 30.60 | 43.20 | 44.80 | 46.00 | 48.10 |
| 43.60 | 46.80 | 43.40 | 42.70 | 43.30 | 45.00 | 46.20 | 48.20 |
| 43.50 | 17.10 | 43.50 | *Empty | 43.40 | 45.00 | 46.40 | 49.70 |
| Average: | | 39.22 | | | | 44.31 | |

*The positive dropout is a result of a BD Viper ™ fluid level error.
No False Positives observed The data included in Tables XVIII through XXIII indicates that amplification reactions were success after storage of the dissolvable film for one month at 2-8° C., 15° C. and 33° C.

While this invention is satisfied by embodiments in many different forms, as described in detail in connection with preferred embodiments of the invention, it is understood that the present disclosure is to be considered as exemplary of the principles of the invention and is not intended to limit the invention to the specific embodiments illustrated and described herein. Numerous variations may be made by persons skilled in the art without departure from the spirit of the invention. The scope of the invention will be measured by the appended claims and their equivalents. The abstract is not to be construed as limiting the scope of the present invention, as its purpose is to enable the appropriate authorities, as well as the general public, to quickly determine the general nature of the invention. In the claims that follow, unless the term "means" is expressly used, none of the features or elements recited therein are intended to be construed as means-plus-function limitations pursuant to 35 U.S.C. §112, ¶6.

We claim:

1. A method of trapping a first substance in a container, the method comprising:
    (i) providing a container having a bottom and a film readily dissolvable in a predetermined substance;
    (ii) introducing the first substance into the bottom of the container, wherein the first substance comprises magnetically responsive particles; and
    (iii) introducing the film down into the container such that the film overlies the first substance in a manner such that it traps the first substance at the bottom of the container thereby preventing dislocation of the first substance from under the film.

2. The method of claim 1, wherein the film has a shape comprising at least one of: planar; solid polygon; hollow polygon; spherical; cubic; oval; capsule-shaped; tablet shaped; and an oblong body.

3. The method of claim 1, wherein the film is formed from a material comprising at least one of: hydroxyalkylmethyl cellulose; carboxymethyl cellulose; carboxylic hydroxyalkyl ester monomer; ethoxylated hydroxyalkyl (meth)acrylate; propoxylated hydroxyalkyl (meth)acrylate; polyethylene glycol (PEG); polyvinyl alcohol (PVA); and combinations thereof.

4. The method of claim 1, wherein the film comprises a fragrance.

5. The method of claim 1, wherein the first substance further comprises at least one of: a lysing agent; a protein denaturant; an aprotic solvent; an alkaline agent; a neutralization buffer; a salt; a metal; an enzyme; an oligonucleotide; a primer; a nucleic acid; a protein; a stabilization component or a media component and combinations thereof.

6. The method of claim 1, wherein the magnetically-responsive particles are composed of at least one of: iron oxide; ferric hydroxide; ferrosoferric oxide; iron sulfide; and iron chloride.

7. The method of claim 1, wherein the container comprises at least one of: an open tube; a closed tube having a bottom; a microwell; an array of microwells; a bottle; and a petridish.

8. The method of claim 1, wherein step (iii) further comprises locating the film over an opening in the container, engaging the film with a moveable plunger, and forcing the film through the opening and into the container by moving the plunger in a first longitudinal direction relative to the container.

9. The method of claim 8, wherein the film is in the form of a segment dimensioned to span the opening in the container.

10. The method of claim 8, wherein the film is in the form of a continuous web or roll, and step (iii) further comprises feeding the film over the opening in the container, and severing a portion of the film from the roll upon introduction into the container.

11. The method of claim 8, wherein step (iii) further comprises locating the film over an opening in the container, and introducing the film into the container via gravity feed.

12. The method of claim 8, wherein step (iii) further comprises locating the film over an opening in the container, and introducing the film into the container via at least one of positive and vacuum pressure.

13. The method of claim 1, further comprising: (iv) introducing a material or mixture into the container.

14. The method of claim 13, wherein the material or mixture comprises at least one of: cells; microorganisms; nucleic acids; proteins; lipids; carbohydrates;
    and combinations thereof.

15. The method of claim 13, wherein the material or mixture comprises a biological sample.

16. The method of claim 15, wherein the biological sample comprises at least one of: urine; clinical urine; vaginal swabs; and combinations thereof.

17. The method of claim 15, further comprising:
    (v) dissolving the film; and
    (vi) creating a mixture comprising the first substance and the biological sample.

18. The method of claim 17, further comprising:
    (vii) binding the first substance and at least portions of nucleic acids present in the biological sample together thereby forming complexes;
    (viii) applying a magnetic field to the container, thereby attracting the complexes to a designated area of the container;
    (ix) removing at least a portion of the biological sample from the container;
    (x) removing the magnetic field from the container;
    (xi) disassociating the nucleic acids from the first substance;
    (xii) reapplying the magnetic field to the container thereby attracting the first substance to a designated area of the container; and
    (xiii) removing the nucleic acids from the container.

19. The method of claim 18, further comprising at least one of:
    (xiv) performing an amplification procedure on the nucleic acids; and
    (xv) conducting an assay to detect the presence and/or concentration of a target analyte in the biological sample.

20. The method of claim 19, wherein at least one of steps (i)(xv) are performed by an automated robotic device.

* * * * *